(12) United States Patent
Dong et al.

(10) Patent No.: US 8,717,549 B2
(45) Date of Patent: May 6, 2014

(54) METHODS AND APPARATUS TO DETECT CONTAMINANTS ON A FLUID SENSOR

(75) Inventors: Chengli Dong, Sugar Land, TX (US); Peter S. Hegeman, Stafford, TX (US)

(73) Assignee: Schlumberger Technology Corporation, Sugar Land, TX (US)

(*) Notice: Subject to any disclaimer, the term of this patent is extended or adjusted under 35 U.S.C. 154(b) by 572 days.

(21) Appl. No.: 12/133,787

(22) Filed: Jun. 5, 2008

(65) Prior Publication Data

US 2009/0306897 A1 Dec. 10, 2009

(51) Int. Cl.
*G01N 21/00* (2006.01)

(52) U.S. Cl.
USPC .......................................................... 356/72

(58) Field of Classification Search
USPC .............. 356/72, 73, 326; 73/152.59, 152.31, 73/152.27, 152.22; 166/250.07, 264, 162, 166/100
See application file for complete search history.

(56) References Cited

U.S. PATENT DOCUMENTS

| | | | |
|---|---|---|---|
| 4,912,332 A * | 3/1990 | Siebel et al. ............... | 250/356.1 |
| 5,201,220 A | 4/1993 | Mullins et al. | |
| 5,812,270 A | 9/1998 | Hampton et al. | |
| 5,939,717 A * | 8/1999 | Mullins ......................... | 250/255 |
| 6,643,021 B1 | 11/2003 | Kawamura | |
| 7,937,223 B2 * | 5/2011 | Ciglenec et al. ................ | 702/12 |
| 2003/0134426 A1 * | 7/2003 | Jiang et al. ..................... | 436/121 |
| 2004/0000636 A1 | 1/2004 | Mullins et al. | |
| 2007/0171412 A1 | 7/2007 | Vannuffelen et al. | |
| 2008/0093078 A1 | 4/2008 | Vasques et al. | |

OTHER PUBLICATIONS

International Search Report issued in PCT/US2009/044832 on Feb. 9, 2009, 3 pages.
Written Opinion of the International Searching Authority issued in PCT/US2009/044832 on Feb. 9, 2009, 6 pages.
Examination Report issued in GB1021410.4 on Feb. 10, 2012, 2 pages.
Examination Report issued in GB1021410.4 on May 4, 2012, 3 pages.
Combined Search and Examination Report issued in GB1212193.5 on Aug. 24, 2012, 4 pages.

* cited by examiner

*Primary Examiner* — Tarifur Chowdhury
*Assistant Examiner* — Abdullahi Nur
(74) *Attorney, Agent, or Firm* — John Vereb

(57) ABSTRACT

Methods and apparatus for detecting a coating on a downhole fluid sensor are disclosed. A coating may refer to a solid or liquid film on a sensor interface with the sampled fluid, caused by contaminants. Detecting a coating may be accomplished by determining a sampled fluid type and measuring at least one fluid parameter using one or more downhole fluid sensors. The coating detection further includes determining whether the measured parameters are within ranges corresponding to the determined fluid type. Additionally or alternatively, measured parameter values that remain substantially stable during sampled fluid pumping may also indicate a coated sensor.

18 Claims, 11 Drawing Sheets

1001

| Input Data | Signal | Unit |
|---|---|---|
| FSOD[450] | optical density channel of FS channel at 450 nm | unitless |
| FSOD[570] | optical density channel of FS channel at 570 nm | unitless |
| FSOD[680] | optical density channel of FS channel at 680 nm | unitless |
| FSOD[1070] | optical density channel of FS channel at 1070 nm | unitless |
| FSOD[1290] | optical density channel of FS channel at 1290 nm | unitless |
| FSOD[1600] | optical density channel of FS channel at 1600 nm | unitless |
| GSOD[1603] | optical density channel of GS channel at 1603 nm | unitless |
| GOR | Gas/oil ratio | scf/stb |
| WATF | water fraction | unitless |

1000

```
//comment: constant parameters
Define local constant double variable:
        OD_cutoff=2.5                    } 1002
        Water_high_cutoff=0.5            } 1004
        GOR_cutoff_1=6000
        GOR_cutoff_2=4000                } 1006
        Color_cutoff_f1=-0.00005
        Color_cutoff_f2=0.4              } 1008
        Scattering_low_cutoff=0.2
        Scattering_high_cutoff_3         } 1010
```

```
//comments: the following variables are local variables
Define local double variable: Color_cutoff, Color_check
Define local integer variable: High_scattering (TRUE/FALSE),
                Coated_window_from_color (TRUE/FALSE)
```
} 1012

FIG. 7A

//comments: check if scattering is high for window coating
if      Scattering_high_cutoff>FSOD[1600]>Scattering_low_cutoff and
        Scattering_high_cutoff>GSOD[1603]>Scattering_low_cutoff then
            High_scattering=TRUE
else
            High_scattering=FALSE
end if
⎫
⎬ 1016
⎭

//comments: compute Color_cutoff
if      GOR>GOR_cutoff_1          then
        Color_cutoff=GOR_cutoff_1*Color_cutoff_f1+Color_cutoff_F2
else
        if GOR<GOR_cutoff_2       then
            Color_cutoff=GOR_cutoff_2*Color_cutoff_f1+Color_cutoff_f2
        else
            Color_cutoff=GOR*Color_cutoff_f1+Color_cutoff_f2
        end if
end if
⎫
⎬ 1018
⎭

*FIG. 7B*

```
//comments: color check, check if color absorption is decreasing with
wavelength like a typical oil
if      (FSOD[570]>OD_cutoff    or    FSOD[450]>FSOD[680])    and
        (FSOD[680]>OD_cutoff    or    FSOD[450]>FSOD[815])    and
        (FSOD[815]>OD_cutoff    or    FSOD[450]>FSOD[1070])   and
        (FSOD[1070]>OD_cutoff   or    FSOD[450]>FSOD[1290])   then
             Color_check=FSOD[570]-FSOD[1600]
else
        Color_check=0
end if
```
⎫
⎬ 1020
⎭

```
//comments: check if color is high for window coating
if      Color_check>Color_cutoff   then
             Coated_window_from_color=TRUE
else
             Coated_window_from_color=FALSE
end if
```
⎫ 1022
⎭

```
//comments: GOR showing a gas with high color and scattering indicates
a window coating
//comments: if WATF is higher than cutoff, then it is not likely a window
coating will form
if      GOR>GOR_cutoff_2      and   High_scattering       and
        Coated_window_from_color then
             if      WATF=absent_value     or    WATF<Water_high_cutoff
             then
                     WINDOW_COATING=COATING
             else
                     WINDOW_COATING=NO_COATING
             end if
else
        WINDOW_COATING=NO_COATING
end if
return
```
⎫ 1024
⎭

*FIG. 7C*

METHODS AND APPARATUS TO DETECT CONTAMINANTS ON A FLUID SENSOR

FIELD OF THE DISCLOSURE

This disclosure relates generally to downhole fluid sampling and analysis techniques and, more particularly, to methods and apparatus to detect a coating on a fluid sensor interface.

BACKGROUND

In oil exploration and production, it is advantageous to sample hydrocarbons in a formation to determine the physical and chemical properties of the fluid in the formation during drilling of a borehole. Identifying these properties is important for characterizing a formation and its fluid(s), determining production methods, and designing well completions and topside facilities. To perform testing, drilling equipment may be removed and a downhole tool may be deployed into the borehole to test and/or sample one or more formation fluids at various stations or positions of the tool. Typically, the tested fluids contain impurities or contaminants such as, for example, drilling fluids, cuttings, mud, or different subterranean fluids. During sampling and measuring, impurities or contaminant may tend to adhere to sensor interfaces with the sampled fluid and form a film coating. This coating can significantly alter the measured characteristics of the fluid sample. It is highly desirable to ensure that these impurities are detected, because even small amounts of contaminant may cause an analysis to mischaracterize the sample.

BRIEF DESCRIPTION OF THE DRAWINGS

FIGS. 7A, 7B, and 7C are diagrams illustrating pseudocode to implement an example process to detect a coating on a window of a fluid analyzer.

SUMMARY

Figure 1:
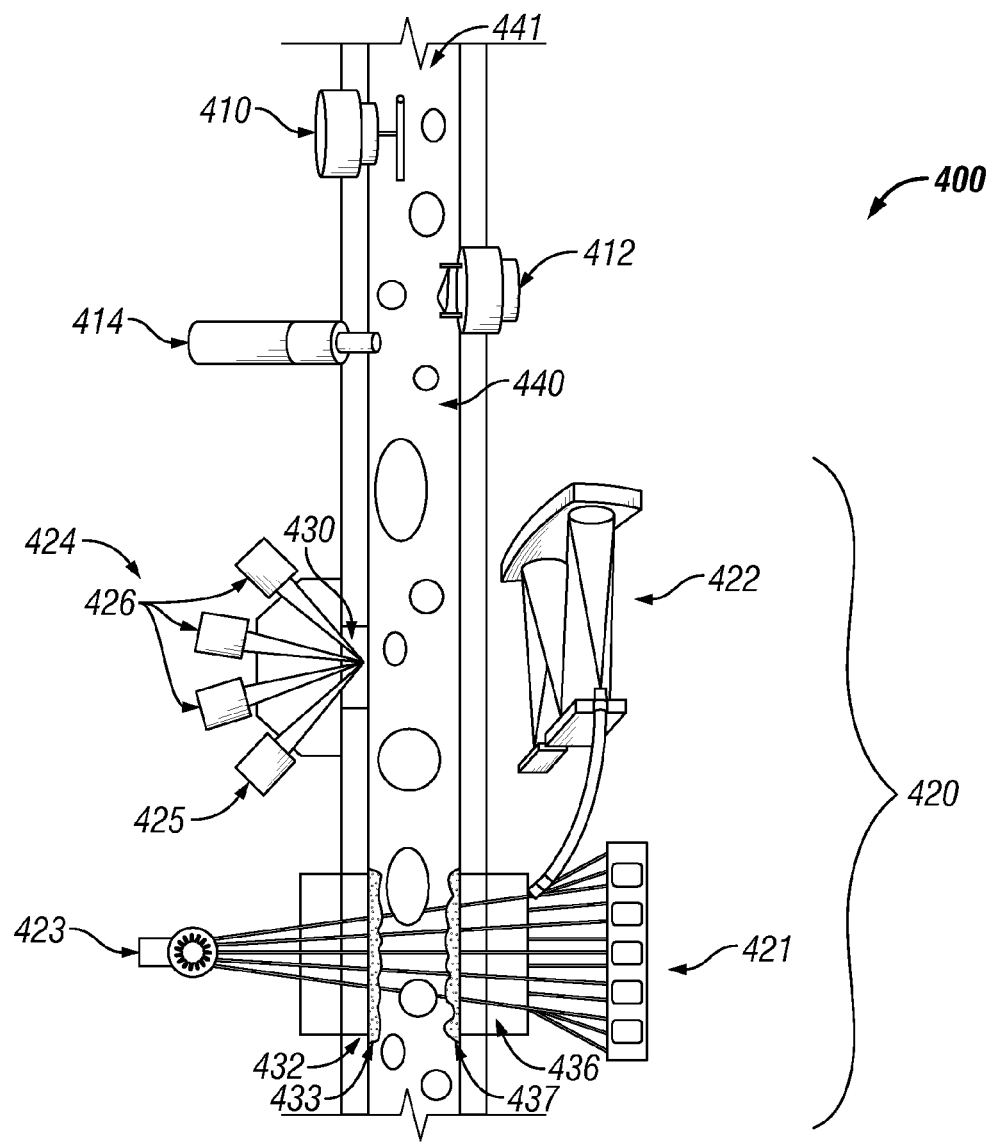
FIG. 1 is a diagram of an example downhole fluid analyzer tool that may be implemented as part of a downhole sampling tool.

In accordance with a disclosed example, a method to detect a coating on a fluid sensor includes determining a fluid sample type, and performing, via the fluid sensor, at least one fluid sample measurement. A determination whether the at least one fluid sample measurement is indicative of a film coating on a fluid sensor interface with the sampled fluid is based on the determination of the fluid sample type.

In accordance with another disclosed example, a method to detect a coating on a window of a fluid analyzer includes measuring an optical density parameter of a fluid sample, a color absorption parameter of the fluid sample for each of a plurality of color channels and a gas/oil ratio of the fluid sample. A determination that there is a coating on the window of the fluid analyzer is based on two or more of the optical density parameter, the color absorption parameters, and the gas/oil ratio of the fluid sample.

In accordance with yet another disclosed example, an apparatus to detect a coating on a fluid sensor comprises a fluid sensor to measure at least one fluid sample parameter and a processing unit. The processing unit determines a fluid sample type, and whether the at least one fluid sample parameter is indicative of a film coating on a fluid sensor interface with the sampled fluid based on the determination of the fluid sample type.

DETAILED DESCRIPTION

In the following detailed description, reference is made to the accompanying drawings, which form a part hereof, and within which are shown by way of illustration specific examples by which the invention may be practiced. It is to be understood that other examples may be utilized and structural changes may be made without departing from the scope of the invention.

Certain examples are shown in the above-identified figures and described in detail below. In describing these examples, like or identical reference numbers are used to identify common or similar elements. The figures are not necessarily to scale and certain features and certain views of the figures may be shown exaggerated in scale or in schematic for clarity and/or conciseness.

The example methods and apparatus described herein may be used to detect a coating on a downhole fluid sensor, for example on a window of a fluid optical spectrometer. A coating in the described examples refers to a solid film, liquid film, or other type of coating caused by downhole fluids, particles, or other impurities or contaminants on a sensor interface with the sampled fluid. Detecting a coating may be accomplished by determining a sampled fluid type (e.g. gas, water, oil, etc) and measuring at least one of a variety of parameters using one or more downhole fluid sensors (e.g. an optical spectrometer, a density/viscosity sensor and/or a reflection/fluorescence sensor). The coating detection further includes determining whether the measured parameters are within ranges corresponding to the determined fluid type. One or more measured parameters that lie outside the ranges indicate a high likelihood of a coated sensor. Additionally or alternatively measured parameter values that remain substantially stable during sampled fluid pumping or unresponsive to the sampled fluid pumping also indicate the likelihood of a coated sensor.

FIG. 1 depicts a block diagram of an example downhole fluid analyzer (DFA) 400 that may implemented, for example, as part of a wireline and/or a while drilling formation sampling tool. In the illustrated example, the DFA 400 may be selectively in fluid communication with a downhole geological formation. Under the action of a pump disposed in the sampling tool, sample fluid 441 extracted from the formation may flow through to analyzer 400 via a flow path or flow line 440, for example in a downward direction.

The DFA 400 is provided with a spectrometer 420 to measure, for example, an optical density (OD), a color absorption, a water fraction, and/or a gas/oil ratio (GOR). For example, the spectrometer 420 may include one or more light sources 423 configured to provide photons having energies corresponding to a particular wavelength range and optical detectors such as a filter array spectrometer 421 and an optional grating spectrometer 422 to determine the intensity of the light sources at the various wavelengths as well as the intensity of light transmitted through fluid samples at those wavelengths. A spectrometer that may be used to implement the example spectrometer 420 to measure the optical densities of formation fluid samples at a plurality of wavelengths is described in U.S. Patent Publication No. 2007/0171412, to Vannuffelen, et al. The spectrometer 420 may generate several data channels, including grating spectrometer data channels and filter array spectrometer data channels, corresponding to values of optical densities measured at each of the plurality of wavelengths. The flowline 440 within the example spectrometer 420 is provided with one or more windows 432, 436 through which light may pass into and out of a fluid sample within the flowline 440. In particular, one or more light sources 423 transmit light through the window into the fluid sample using one or more light paths traversing an interface between the window and the fluid in the flow line 440. Depending on the characteristics of the fluid sample, light energy in certain light wavelengths will be absorbed more readily by the fluid sample than other light wavelengths. The light that is transmitted through the fluid sample is measured by the spectrometer 420, and the measurements may be used to determine the characteristics and/or composition of the fluid sample.

The spectrometer 420 is in line with a reflection/fluorescence sensor 424. In particular, the reflection/fluorescence sensor 424 includes a light source 425 emitting a light beam and a plurality of light detectors 426 to measure, for example, a fluorescence, and/or a reflection of formation fluid samples. The reflection/fluorescence sensor 424 is also provided with a window 430 similar to the windows 432 and 436 of the spectrometer 420. The spectrometer 420 is further in line with a pressure and temperature sensor 414, a resistivity sensor 412, and a density and viscosity sensor 410.

Although the components of FIG. 1 are shown and described above as being communicatively coupled and arranged in a particular configuration, persons of ordinary skill in the art will appreciate that the components of the DFA tool 400 can be communicatively coupled and/or arranged differently than depicted in FIG. 1 without departing from the scope of the present disclosure. Further, in other example implementations in which measurements other than or in addition to the measurements implemented as shown in FIG. 1 are used, the DFA 400 may for example be supplemented with other types of suitable sensors including, for example, NMR sensors, capacitance sensors, etc.

For brevity and clarity, the following examples refer to the window of the spectrometer 420. However, the examples are equally relevant to the window of the reflection/fluorescence sensor 424, the resistivity sensor 412, the density/viscosity sensor 410, or other sensors that may be implemented in the DFA 400. Before or during sampling and measuring, one or both windows 432, 436 of the spectrometer 420 may be exposed to materials (e.g., drilling mud, water, oil) that tend to adhere to the window. An example contaminant is the oil-based drilling muds used in modern drilling, which are miscible with hydrocarbon formation fluids. As samples are collected from the formation, drilling mud may mix with and contaminate the samples. Over time, the amount of drilling mud in the fluid sample is reduced, but the initial high concentrations of drilling mud may leave a coating 433, 437 on the windows 432 and 436, respectively, of the spectrometer 420. Another example contaminant, a medium-weight oil often found in formation fluid, forms a coating on the window of the spectrometer 420. This coating can significantly alter the measured characteristics of the fluid sample. For example, natural gas in the flowline 440 may be mischaracterized, or the spectrometer 420 may be unable to accurately determine when an acceptable fluid sample has been obtained. Detecting a coating on a window of the spectrometer 420 is, therefore, beneficial to obtaining acceptable fluid sample measurements.

Figure 2:
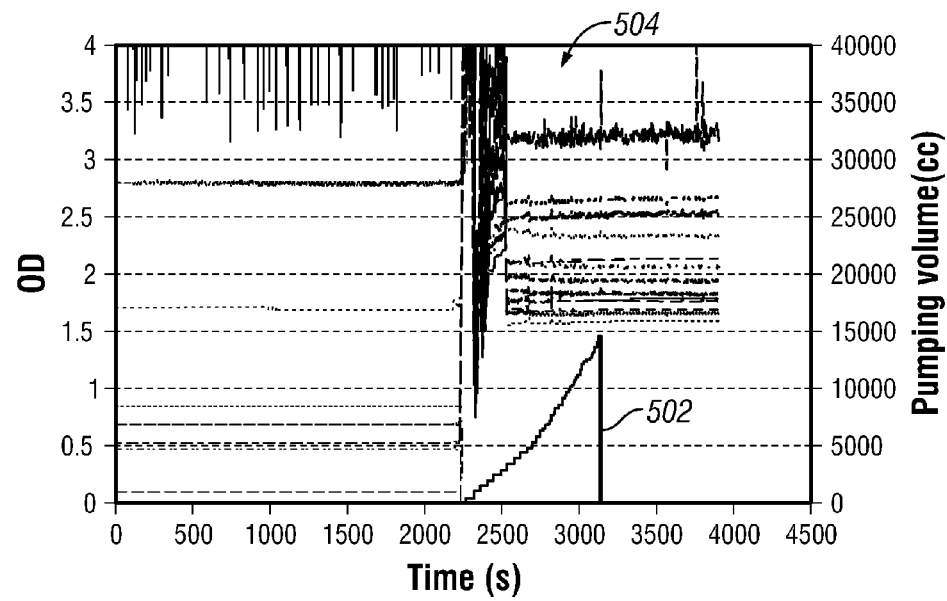
FIG. 2 is a graphical representation of an example optical density measurement of a fluid sample by a spectrometer that has a coating on its window.
Figure 3:
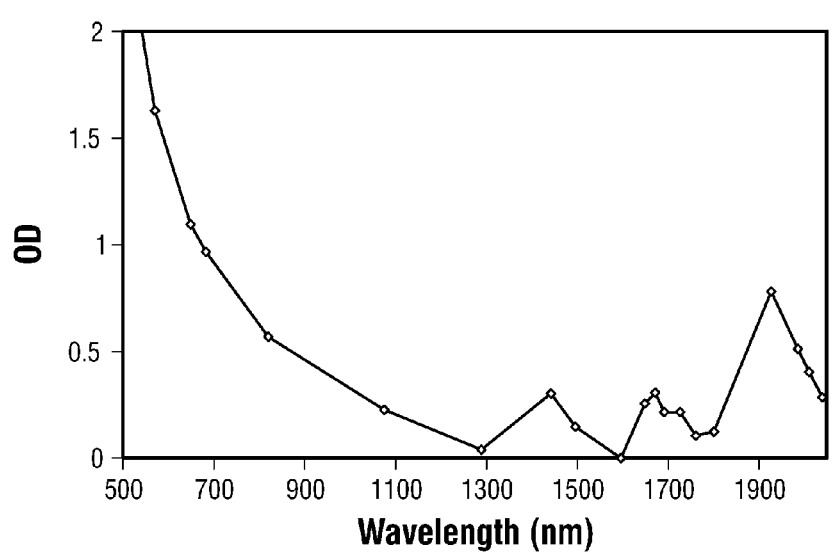
FIG. 3 is a graphical representation of an example absorption spectrum measurement of a fluid sample by a spectrometer that has a coating on its window.
Figure 4:
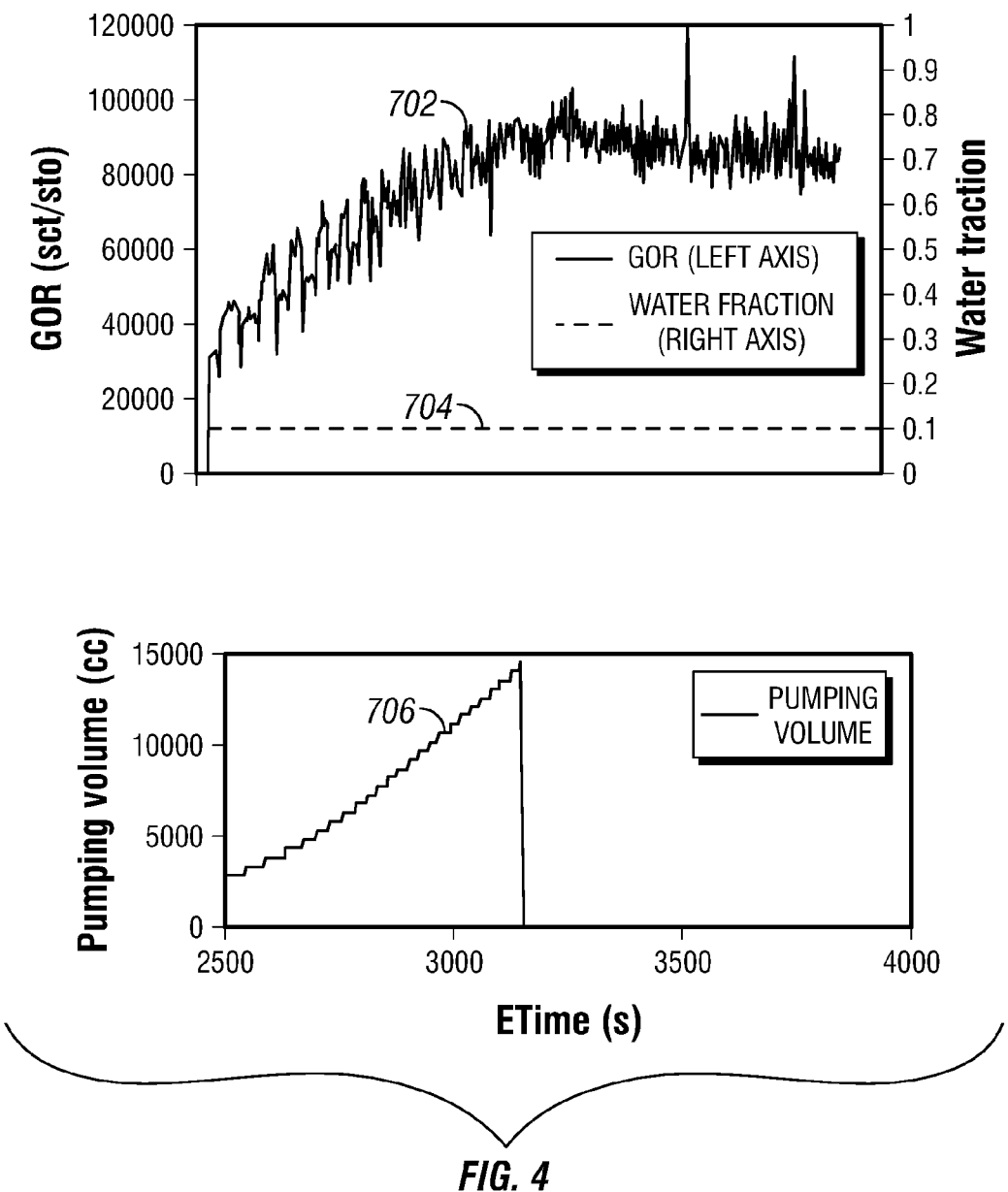
FIG. 4 is a graphical representation of an example water fraction and gas/oil ratio measurement of a gas sample by a spectrometer that has a coating on its window.

As described in greater detail below, to detect a coating on the window of the spectrometer 420, the spectrometer 420 may measure the fluid sample for at least one of a number of parameters. Example parameters that may be measured by the spectrometer 420 include an optical density of the fluid sample, color absorption for each of several color channels, a water fraction of the fluid sample, a gas/oil ratio (GOR) of the fluid sample, or a scattering parameter. In particular, FIGS. 2, 3 and 4 illustrate example graphical representations of parameters that may be measured by the spectrometer 420 when a gas is extracted from an underground formation and when one or both windows 432, 436 are coated with an oil and/or a water film that is not representative of the sampled gas. While these example graphical representations relate to gas sampling and parameters measured via the spectrometer 420, it should be appreciated that the scope of the present disclosure is not limited to gas sampling and/or parameters measured by a spectrometer.

FIG. 2 is a graphical representation of an example optical density measurement of a fluid sample by a spectrometer that has a coating on its window. Optical density is a unitless measure of light transmittance as described by equation 1:

$$OD = -\log \frac{I}{I_0} \quad \text{(Eq. 1)}$$

where I is the transmitted light and $I_0$ is the incident light in the spectrometer. An optical density of zero indicates that no light is absorbed (i.e., 100% is transmitted), an optical density of 1.0 indicates that 10% of the light is transmitted through the sample, an optical density of 2.0 indicates that 1% of light is transmitted through the sample, etc. The example graph shows a total pumped volume 502 and several optical density measurements 504 for corresponding filter channels over time. In the example measurements, the flowline contains natural gas, which has a relatively low optical density. Typically, a high optical density (e.g., from particle scattering) varies significantly with pumping, and the optical density variations are synchronized with pump strokes (i.e., increases as the pump displaces fluid through the flowline). However, when the window of the spectrometer is coated, the spectrometer may measure a high optical density across all or almost all channels, and the optical density is substantially unresponsive (e.g., unvarying relative) to pumping of the fluid through the flowline.

FIG. 3 is a graphical representation of an example absorption spectrum measurement of a gas sample (e.g., GOR>100,000 cubic feet per stock tank barrel (scf/stb)) by a spectrometer that has a coating on its window. A color spectrum in the described examples refers to the portion of a measured spectrum in the visible range, e.g. below 1000 nm (nanometer) wavelength. As mentioned above, because natural gas has little or no color, color absorption measurements of natural gas are typically very low when the spectrometer window has no coating. However, as shown in FIG. 3, the optical density for each color channel is relatively high. Further, the color absorption pattern from the measurements is similar to a color absorption pattern for a medium-weight oil. That is, for a selected color absorption wavelength region, the color absorption or optical density in the shorter-wavelength channels is higher than the color absorption or optical density in the longer-wavelength channels (e.g. the optical density decreases exponentially with the wavelength). The medium-weight oil-type pattern measurement for a gas sample may indicate a coated window. It should be recognized that various substances or materials may present different color absorption patterns, and method of detecting those substances or materials may be modified to take into account the characteristics of such materials or substances.

FIG. 4 is a graphical representation of an example water fraction measurement and a GOR measurement of a gas sample. The water fraction is a ratio of volume of water in a sample to the total volume of the sample. The example graph shows the measured GOR 702, the measured water fraction 704, and the total pumped fluid 706 over time. A typical gas sample cannot carry a stable fraction of large amounts of water during pumping, except for a small amount of vaporized water. A typical gas sample, in the absence of window coating, would be expected to have at most a small water fraction, such as 0.01 or less. If a window coating contains water, the coating can show a stable water fraction that is much greater than a typical water fraction for a gas.

The observations discovered by the inventors of the present disclosure and illustrated in FIGS. 2, 3 and 4 can be used to advantage for detecting a coating on the window of the spectrometer 420, as further detailed below in the description of FIGS. 5, 6 7A and 7B. While the example methods and implementations in FIGS. 5, 6, 7A and 7B relate to gas sampling and the utilization of parameters measured via the spectrometer 420, it should be appreciated that the scope of the present disclosure is not limited to gas sampling and/or parameters measured by an optical spectrometer.

Figure 5:
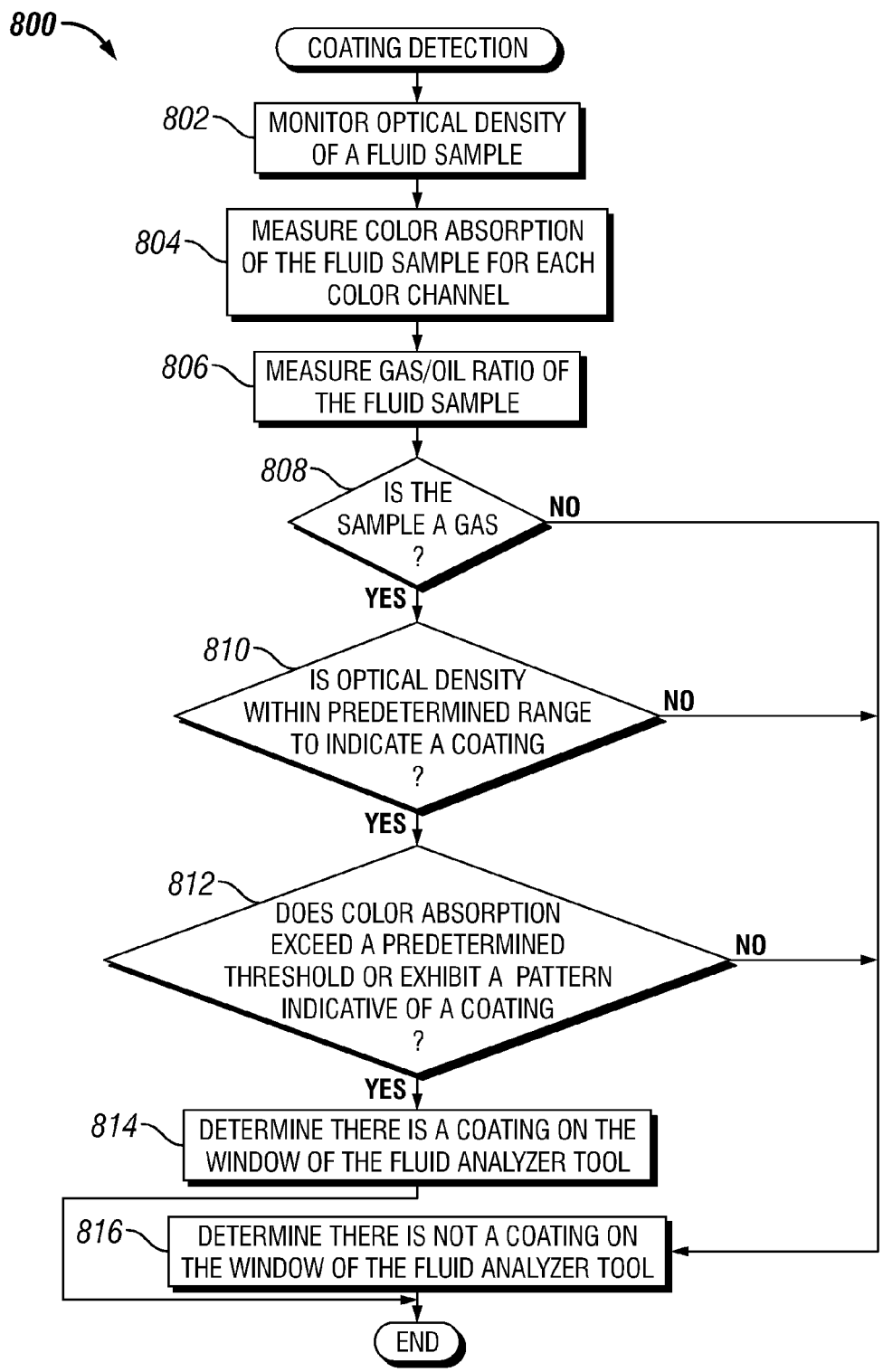
FIG. 5 is a flowchart depicting an example process to detect a coating on a window of a fluid analyzer.

FIG. 5 is a flowchart depicting an example process 800 to detect a coating on the window of a fluid analyzer. The process 800 may be implemented using, for example, the downhole fluid analyzer 400 of FIG. 1.

The example process 800 begins by measuring an optical density parameter of a fluid sample (block 802). The fluid sample may be located in the flowline 440 passing through the spectrometer 420. The measured optical density may be the product of particle scattering as light penetrates the fluid sample and is measured by the spectrometer 420.

The process 800 then measures a color absorption parameter of the fluid sample using the spectrometer 420 (block 804). The color absorption parameter may include several measurements to measure color absorption at several color channels. Each color channel corresponds to a particular light wavelength or a range of light wavelengths, and measuring each color channel includes determining an optical density of the fluid sample for each color channel. The measured color absorption parameters for the channels may be used collectively to determine a pattern, or the parameters may be processed to determine one or more color absorption parameters.

The process 800 continues by measuring a GOR parameter of the fluid sample at the spectrometer 420 (block 806). The GOR parameter may be used to determine whether the fluid sample is a liquid or a gas. However, it should be recognized that alternative methods may be used to determine whether the fluid sample a fluid type. The alternative methods includes, but are not limited to, prior knowledge from an offset well, pressure gradient measurements, or fluid sample compressibility as indicated during pumping, etc. . . . .

When the parameters of the fluid sample have been measured by the spectrometer 420, the process 800 (e.g., via a processing unit) determines whether there is a coating on the window of the spectrometer 420 by testing the parameters. The processing unit first determines whether the GOR parameter indicates that the fluid sample is a gas (block 808). For example, if the GOR is greater than a predetermined threshold, the fluid sample is a gas. If the fluid sample is a gas, the processing unit determines whether the measured optical density parameter is within a predetermined range to indicate a coating on the window of the spectrometer 420 (block 810). For example, the processing unit may determine the optical density is indicative of a coating if the optical density of the fluid sample is higher than the optical density for a typical gas. If the optical density parameter is indicative of a coating, the processing unit continues by determining whether the measured color absorption parameters are indicative of a coating (block 812). The processing unit may determine that the color absorption parameters are indicative of a coating if the color absorption parameters exhibit a pattern similar to a known substance (e.g., water, crude oil), or if the color absorption parameters have relatively high optical densities for each color channel.

If the processing unit determines that the fluid sample is a gas, and that the optical density and color absorption parameters are indicative of a coating, then the processing unit determines that there is a coating on the window of the fluid analyzer tool 400 (block 814). Because the fluid sample is a gas and high optical density values and high color absorption values are not typical for a gas, high values are contradictory to the presence of gas in the flow line as indicated by a high GOR measured at block 808. In other words, contradictory measurement values may be used by the processing unit to determine that the window is coated.

If at any of blocks 810, and/or 812, a measured parameter is determined to be not indicative of a coated window, the processing unit determines that there is not a coating on the window of the fluid analyzer 400 (block 816).

Figure 6:
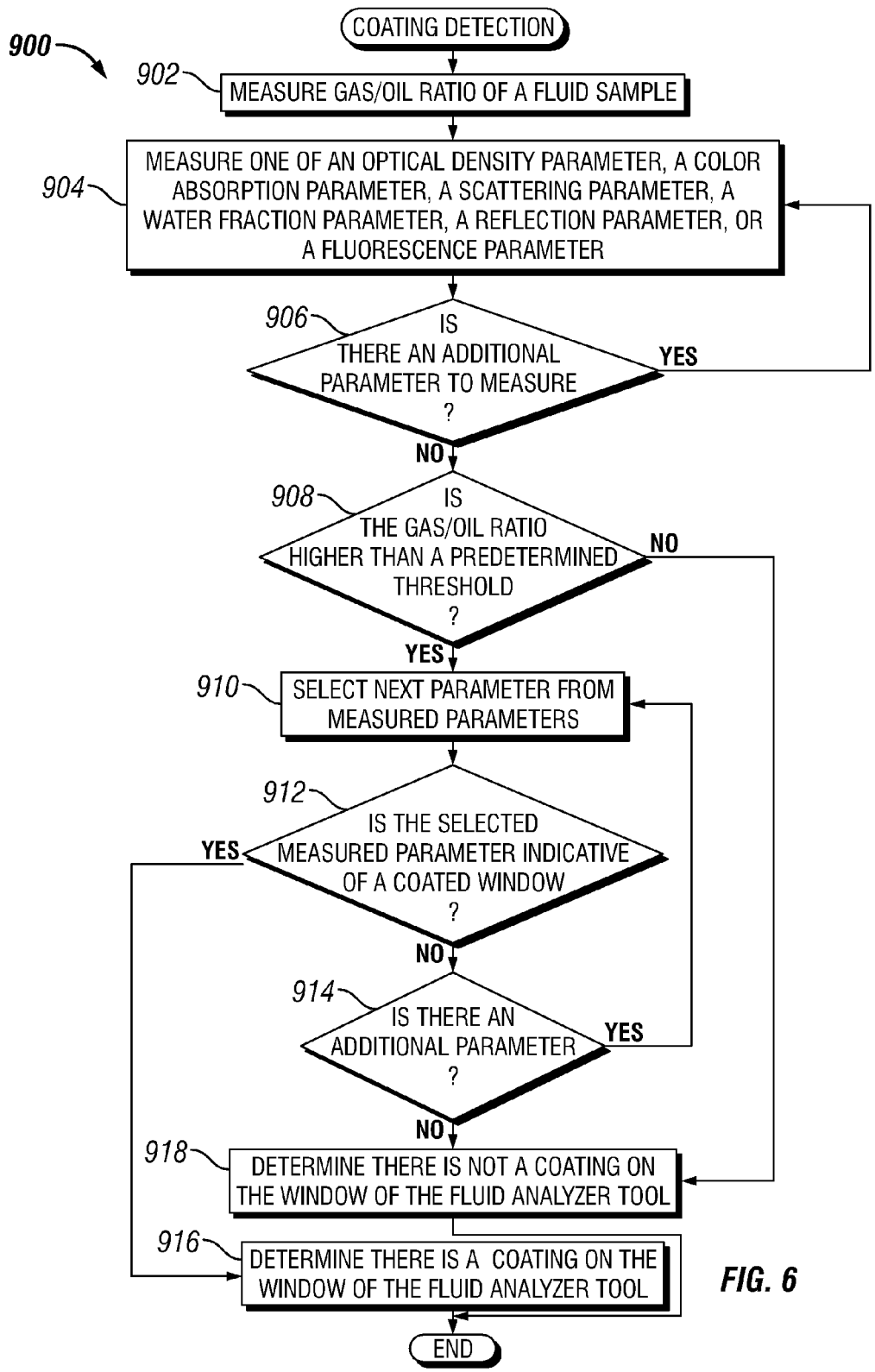
FIG. 6 is a flowchart depicting another example process to detect a coating on a window of a fluid analyzer.

FIG. 6 is a flowchart depicting another example process 900 to detect a coating on the window of the fluid analyzer 400. The process 900 determines whether the fluid sample is a gas, and measures at least one of several possible parameters to determine whether there is a coating on the window. The example process 900 begins by measuring the GOR of the fluid sample (e.g., via the spectrometer 420) at block 902. The process 900 continues by measuring one of several parameters, such as optical density, color absorption, scattering, or water fraction (block 904). A scattering parameter in the described examples refers to a light absorption (e.g. a large optical density) at a wavelength or in a wavelength region at which fluids encountered downhole have usually a low absorption. Thus, a scatting parameter may be indicative of the presence of a solid film or fine particles having coated one or more window of the spectrometer 420. An example wavelength or wavelength region in which fluids encountered downhole have usually a low absorption is around 1600 nm (nanometers). The process 900 then determines whether there is an additional parameter that may be measured that may provide a further indication of whether there is a coating on the window of the fluid analyzer 400 (block 906). If there is another parameter to be measured, control returns to block 904 to measure the parameter. The process 900 may continue to measure parameters using the loop of blocks 904 and 906 until all desired or available parameters have been measured.

When there are no remaining parameters to be measured (block 906), the process 900 determines whether the fluid sample is a gas based on whether the gas/oil ratio is higher than a predetermined threshold (block 908). It should be noted that blocks 902 and 908 may be modified to accommodate additional or alternative methods of determining whether the fluid sample is a gas. If the process 900 determines that the fluid sample is a gas (block 908), a measured parameter is selected from the measured parameters (block 910). The process 900 then determines if the selected measured parameter is indicative of a coated window (block 912). For example, the process 900 may determine that an optical density parameter is within a range to indicate that the window is coated as described above. If the selected measured parameter is not indicative of a coated window (block 912), the process 900 determines whether there is an additional measured parameter (block 914). If there is an additional measured parameter, control returns to block 910 to select the next measured parameter (i.e., a measured parameter that has not previously been selected).

If the GOR is higher than the threshold (i.e., the fluid sample is a gas) and any of the measured parameters indicate a coated window, the example process 900 determines that there is a coating on the window of the fluid analyzer 400 (block 916). However, if the process 900 determines at block 908 that the fluid sample is not a gas or determines at block 914 that there are no remaining measured parameters, the process 900 determines that there is not a coating on the window of the fluid analyzer 400 (block 918). For the example process 900 to determine that there are no remaining measured parameters (block 914), all selected measured parameters must be determined by the process 900 to be not indicative of a coated window. Otherwise, the process 900 will determine at block 912 that one of the measured parameters is indicative of a coated window and, therefore, will determine at block 916 that the window is coated.

However, the example process 900 may be modified to permit a number of measured parameters to be indicative of a coated window and still determine that the window is not coated. Further, the example process 900 may additionally or alternatively be modified to require and/or reject one or more of the example parameters or other parameters.

FIGS. 7A, 7B, and 7C are diagrams illustrating pseudocode to implement an example process 1000 to detect a coating on a window of a fluid analyzer. The example pseudocode may be implemented using any programming language to cause a processing unit to perform a process to detect the coating. A signal table 1001 defines the input and output signals used by the example pseudocode. An example signal defined in the signal table 1001 is the FSOD[450] signal, which is an optical density measurement from a filter array spectrometer (FS) channel at a 450 nanometer (nm) wavelength in an in situ fluid analyzer (IFA). Another example signal is the GSOD[1603] signal, which is an optical density measurement from a grating spectrometer (GS) channel at a 1603 nm wavelength. The input signals may be received from a spectrometer (e.g., the spectrometer 420 of FIG. 2), and the output signal may be used to initiate a process to remove a coating from the window of the spectrometer 420.

The process 1000 may then check to see if any of the parameters have not been measured by the spectrometer (e.g., the spectrometer 420 of FIG. 1) at 1014. The process 1000 may tolerate that one or more parameter (e.g. he water fraction WATF) not be measured. Thus, the pseudocode may be modified to tolerate absent measurements depending on the application.

The pseudocode begins by defining predetermined parameters and/or ranges for optical density 1002, water fraction 1004, GOR 1006, color absorption 1008, and scattering 1010. These ranges are used by the process 1000 to determine whether the measured parameters are indicative of a coated window. Although certain parameters are shown in the example pseudocode, it should be recognized that the parameters may be added, subtracted, or changed to accommodate particular fluid types, drilling techniques, or any other variable that may affect the ranges of measured parameters. Next, local variables are established at 1012 to define placeholders for calculated values and decisions.

Next, the process 1000 determines a scattering parameter (1016) by determining whether the FSOD[1600] channel measurement and GSOD[1603] channel measurement are both within the predetermined scattering range (e.g., 0.2 and 3). If the measurement values for both channels are within the range, the process 1000 determines that there is high scattering in the fluid sample and stores the decision in a variable. Otherwise, the process 1000 determines that there is not high scattering and stores the decision in a variable. As previously disclosed, high scattering may be indicative of the presence of coating of the spectrometer window by a film of dried mud, solid particles, etc . . . .

The process 1000 then computes a wavelength range for selecting the color absorption parameters based on the GOR parameter at 1018. If the GOR is too high (e.g., greater than 6000 scf/stb), the process 1000 uses a maximum GOR value to compute the color absorption range. Similarly, if the GOR is too low (e.g., less than 4000 scf/stb), the process 1000 uses a minimum GOR value to compute the color absorption range. However, if the measured GOR is within the maximum and minimum GOR values, the measured GOR is used to compute the color absorption range.

The color absorption range is then used to determine whether the color absorption of the fluid sample is indicative of a coated window (1020). The example process 1000 tests, for each channel FSOD[570], FSOD[680], FSOD[815], and FSOD[1070], whether the optical density for the channel is greater than the predetermined threshold, or whether the optical density for the next channel (e.g., FSOD[680] for FSOD [570], etc.) is less than optical density of the lowest-wavelength channel FSOD[450]. The first condition tests whether the optical density for a channel is too high to indicate a gas. The second condition tests whether the color absorption follows a pattern indicative of, for example, another fluid that may be located in the fluid formation.

If at least one of the conditions is true for every tested channel, then the process 1000 calculates a color absorption parameter from the measured FSOD channels. Otherwise, the process sets the color absorption parameter to a value that is not indicative of a coating on the window of the spectrometer 420.

Next, the example process 1000 compares the color absorption parameter to the calculated color absorption range (1022). If the color absorption parameter is outside of the color absorption range, the process 1000 determines that the color absorption is indicative of a coating on the window, and stores the decision in a variable. Otherwise, the process 1000 determines that the color absorption is not indicative of a coating, and stores this decision in a variable.

When all of the indicators have been determined, the process 1000 determines whether there is a coating on the window based on whether the parameters described above are indicative of a coating. The process 1000 examines the GOR to determine if the sampled fluid is a gas. In this case, the process 1000 determines if either the scattering parameter or the color parameter is contradictory with the presence of gas in the flow line and is thus indicative of a coated window. In addition, the water fraction, if measured, is also included in the process. A water film may be detected by a measured water fraction measured below a predetermined threshold. Indeed, a water film coating translates usually in a low water fraction because the film thickness is small. Larger water fractions are usually indicative of water in the sampled fluid and are not indicative of a window coating.

In particular, if the process 1000 determines that the GOR is not too low, that there is high scattering, that the color absorption parameter is indicative of a coating, and that the water fraction parameter is not too high, then there is a coating on the window of the spectrometer 420. The process 1000 may determine that the water fraction parameter is not too high if the water fraction is not measured (i.e., is an absent value) or if the water fraction parameter is within a predetermined range. If the process 1000 determines that there is a coating on the window, the decision is stored in a variable (e.g., WINDOW_COATING). This variable may be used by another process to, for example, initiate a process to remove the coating. One particular process that may be used to remove a coating on the window is described in U.S. Patent Publication 2008/0093078, which is incorporated herein in its entirety.

In contrast, the example process 1000 determines that there is no coating if the parameters are not indicative of a coating. It should be noted that the determination criteria may be modified depending on the application. For example, the process 1000 may be modified to be more sensitive to a coating by not requiring all of the parameters calculated in the example process 1000 to be indicative of the coating. Other modifications may be made as appropriate.

While particular parameters are used in the example methods 800 and 900 and/or the example process 1000, it should be recognized that other spectrometer parameters may be used alone or in combination to determine that a fluid sample is a gas. Also, it should be recognized that other spectrometer parameters may be used alone or in combination to determine that a sensor interface with the sampled fluid is coated, for example by determining that there are measurements contradictory with the presence of gas in the flow line of the DFA 400.

Further, multiple sensors and/or parameters may be used to modify the example process 800, 900 and 1000 for the purpose of detecting a gas in the flow line. In particular, alternative methods include measuring fluid parameters with one or more sensors of the fluid analyzer 400, other than the spectrometer 420 that, in some cases, may be free of and/or less sensitive to coating by a film of contaminant. For example, gas may be detected using the intensity of the reflected light as measured by the reflection/fluorescence sensor 420, as taught for example in U.S. Pat. No. 5,201,220, or by a low density and low viscosity values as measured by the density/viscosity sensor 410. Alternatively, parameters measured by the spectrometer 420 may be used to determine that the sampled fluid is a gas (e.g. a GOR parameter), and the process 800, 900 and 1000 may be modified to determine that one or more sensor interfaces, other than the spectrometer window, are coated. In one example, a high GOR measured by the spectrometer 420 and a high fluid density (e.g. larger than 0.9 g/cc) and/or a high fluid viscosity (e.g. larger than 1 cP) measured by the density/viscosity sensor 410 may be indicative that the interface of the density/viscosity sensor 410 is coated. In another example, a high GOR measured by the spectrometer 420 and the absence of reflected light (less than 7% intensity) above a critical angle of incidence may be indicative a the presence of coating on the window 430 of the reflection/fluorescence sensor 424.

Still further, although the particular parameters of the example methods 800 and 900 and/or the example process 1000 that are used to make the determination that a fluid sample is a gas, it should be recognized that other parameters may be used alone or in combination to more generally determine a type of the sample fluid (e.g. water, oil, gas). In another example implementation, water sample may be detected by a high density value e.g. larger than around 1 g/cc) and a low viscosity value (e.g. lower than around 1 cP) as measured by the density/viscosity sensor 410, and/or by a low resistivity value (lower than around 10 ohm m) as measured by the resistivity sensor 412. In yet another implementation, liquid oil sample may be detected by a low GOR value (e.g. lower than around 4000 scf/stb) measured by the spectrometer 420. In these implementations, the example methods 800 and 900 and/or the example process 1000 may be modified to measure a second fluid parameter with the DFA 400 and determine if the measured value is contradictory with the sampled fluid type. A contradictory value may in turn be indicative that the interface of the sensor used to measure the second fluid parameter is coated. For example, if an optical density measured in an oil peak by the spectrometer 420 is larger than a predetermined threshold and/or is substantially unresponsive (e.g., unvarying relative) to pumping through the flowline of a fluid identified as water, this may indicate that the window of the spectrometer is coated with oil. In another example, if a scattering parameter measured by the spectrometer 420 is larger than a predetermined threshold and/or is substantially unresponsive to pumping of a fluid identified as water, oil or gas through the flowline, this may indicate that the window of the spectrometer is coated with solid particles.

Figure 8:
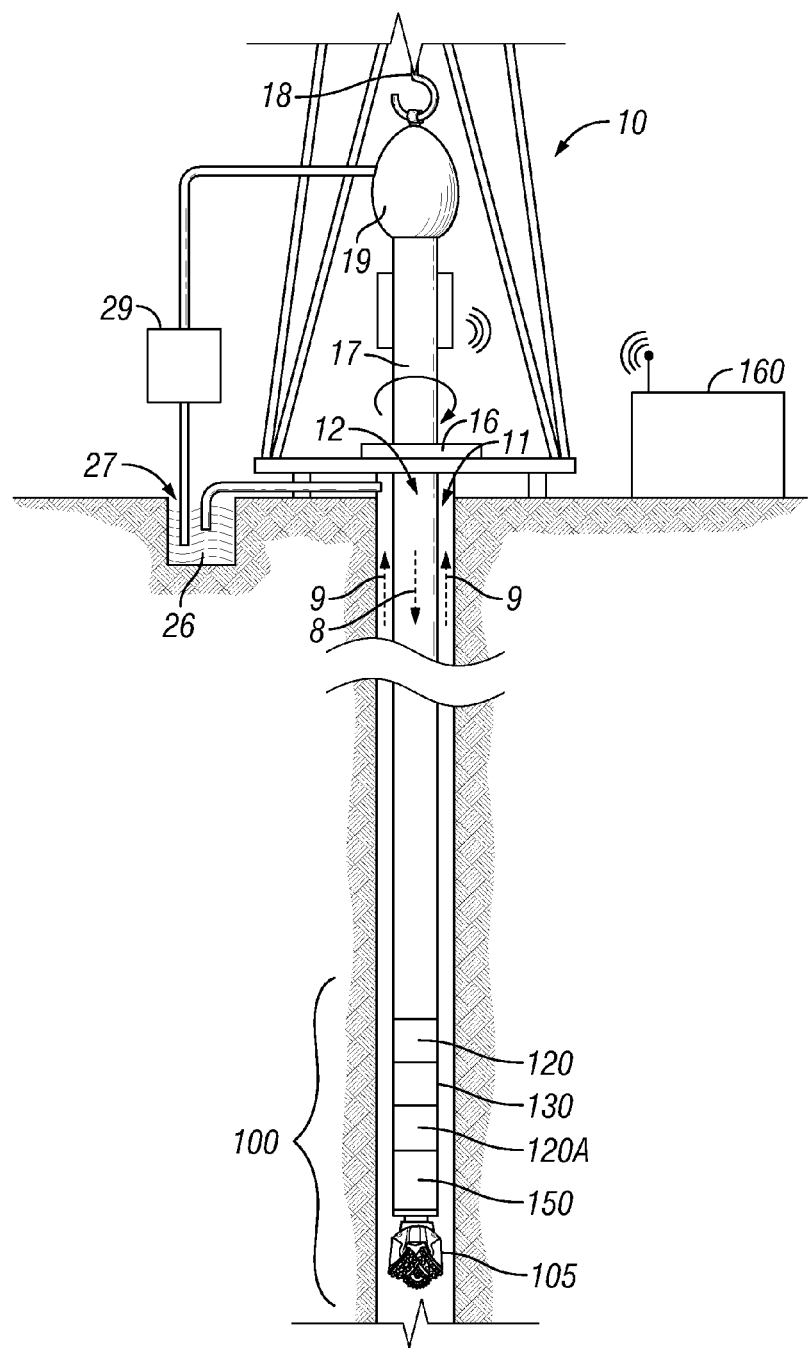
FIG. 8 illustrates a wellsite system in which the example methods and apparatus can be implemented.

FIG. 8 illustrates a wellsite system in which the example methods and apparatus described herein can be implemented. The wellsite can be onshore or offshore. In this exemplary system, a borehole 11 is formed in subsurface formations by rotary drilling in a manner that is well known. In other example implementations, the example methods and apparatus can be implemented in a directional drilling system, as described below.

A drill string 12 is suspended within the borehole 11 and has a bottom hole assembly 100 which includes a drill bit 105 at its lower end. The surface system includes platform and derrick assembly 10 positioned over the borehole 11. The assembly 10 includes a rotary table 16, a kelly 17, a hook 18 and a rotary swivel 19. The drill string 12 is rotated by the rotary table 16, energized by means not shown, which engages the kelly 17 at the upper end of the drill string 12. The drill string 12 is suspended from the hook 18, attached to a traveling block (also not shown), through the kelly 17 and the rotary swivel 19, which permits rotation of the drill string 12 relative to the hook 18. As is well known, a top drive system could alternatively be used.

This example further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 105 and circulates upwardly through the annulus region between the outside of the drill string 12 and the wall of the borehole 11 as indicated by the directional arrows 9. In this well-known manner, the drilling fluid lubricates the drill bit 105 and carries formation cuttings up to the surface as it is returned to the pit 27 for recirculation.

The bottom hole assembly 100 of the illustrated example includes a logging-while-drilling (LWD) module 120, a measuring-while-drilling (MWD) module 130, a roto-steerable system and motor 150, and the drill bit 105. The LWD module 120 is housed in a special type of drill collar, as is known in the art, and can contain one or a plurality of known types of logging tools. It will also be understood that more than one LWD and/or MWD module can be employed, e.g. as represented at 120A. References, throughout this description, to a module at the position of reference numeral 120 can alternatively mean a module at the position of 120A. The LWD module 120 includes capabilities for measuring, processing and storing information, as well as for communicating with the MWD module 130. In the present example, the LWD module 120 includes a fluid sampling device, such as one or more pumps. In addition, the LWD module includes a fluid analyzer module having one or more fluid sensor such as an optical fluid analyzer, a fluid density/viscosity sensor, etc.

The MWD module 130 is also housed in a special type of drill collar, as is known in the art, and can contain one or more devices for measuring characteristics of the drill string 12 and the drill bit 105. The MWD module 130 further includes an apparatus (not shown) for generating electrical power to the downhole system. This may typically include a mud turbine generator powered by the flow of the drilling fluid, it being understood that other power and/or battery systems may be employed. In the present example, the MWD module 130 may include one or more of a weight-on-bit measuring device, a torque measuring device, a vibration measuring device, a shock measuring device, a stick slip measuring device, a direction measuring device, and an inclination measuring device. The MWD module 130 further includes capabilities for communicating with the surface equipment.

The example system of FIG. 8 also includes a logging and control system or unit 160, which may be used to control the operations of the drill string 12, the MWD module 130, the LWD module 120, etc. Additionally, the logging and control system 160, and/or a downhole control system disposed in the LWD module 120 (e.g. a controller and/or processing system 230 of FIG. 9) may be configured or programmed to perform some or all of the operations associated with the example methods of FIGS. 5, 6, 7A, and 7B.

Figure 9:
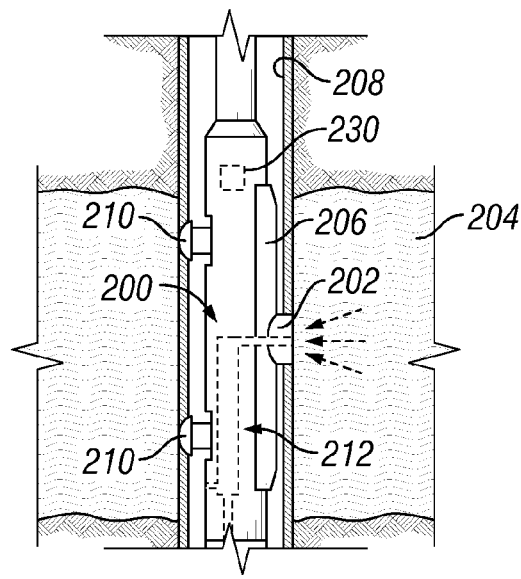
FIG. 9 is a simplified diagram of a sampling-while-drilling logging device.

FIG. 9 is a simplified diagram of a sampling-while-drilling logging device or tool 200 (such as a type described in U.S. Pat. No. 7,114,562, incorporated herein by reference), which may be utilized as the LWD tool 120 or part of an LWD tool suite. The tool 200 is provided with a probe 202 for establishing fluid communication with the formation and drawing the fluid from a formation 204 into the tool 200, as indicated by the arrows. The probe 202 may be positioned in a stabilizer blade 206 of the tool 200 and extended therefrom to engage a borehole wall 208. The stabilizer blade 206 includes one or more blades that are in contact with the borehole wall 208. Backup pistons 210 may also be provided to assist in applying force to push the tool 200 and/or probe 202 against the borehole wall 208.

The fluid 204 may be drawn into the tool 200 via the probe 202, using for example a pump (not shown). In the illustrated example, a fluid analyzer module 212 may be similar to the DFA 400 of FIG. 1. For example, the fluid analyzer module includes a spectrometer to measure, among other things, the optical density (OD) of formation fluid samples. In other example implementations in which measurements (e.g., density measurements, nuclear magnetic resonating (NMR) measurements, resistivity measurements, capacitance measurements, etc.) other than or in addition to OD measurements are used, the fluid analyzer module 212 may be replaced or supplemented with other types of suitable sensors (e.g., a reflection/fluorescence sensor, NMR sensors, density sensors, resistivity sensors, capacitance sensors, etc.).

During the early phase of a sampling operation, relatively large concentrations of drilling muds or fluids may be present in the fluid sample, resulting in measurements that indicate the fluid sample is not representative of the formation fluid. As more fluid is pumped into the tool 200, the concentration of drilling fluid is reduced. Eventually, a fluid sample is obtained that may be identified by at least one fluid sensor of the fluid analyzer module 212 as characteristic or representative of the formation fluid. Additionally, the tool 200 may be provided with devices, such as sample chambers, for collecting fluid samples for retrieval at the surface.

Figure 10:
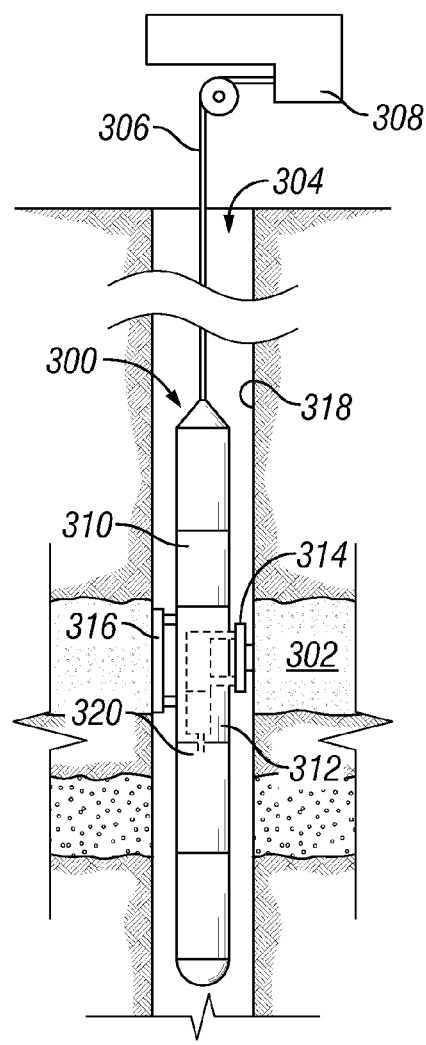
FIG. 10 is a simplified diagram of a wireline formation testing device.

FIG. 10 is a simplified diagram of a wireline formation testing tool 300 that may be used to withdraw, measure characteristics of, and/or analyze fluid samples present in a geological formation 302. The example formation testing tool 300 of FIG. 10 may be used to, among other things, implement the example methods and apparatus described herein. The example tool 300 is suspended in a borehole (i.e., a well) 304 from the lower end of a conveyance 306 such as a wireline or multiconductor cable, that is spooled from the surface. At the surface, the example wireline 306 is typically connected to an example controller and/or processing system 308 that monitors and/or controls the tool 300. The example controller and/or processing system 308 of FIG. 10 and/or a controller and/or processing system 310 implemented by and/or within the tool 300 may, additionally or alternatively, perform fluid composition analyses based on one or more measurements (e.g., optical density measurements) made by and/or within the sampling tool 300 (e.g., by a fluid analyzer module 312, similar to the DFA 400 of FIG. 1). As will be appreciated by those skilled in the art, the example controllers 308 and 310 of FIG. 10 may include one or more microprocessors or other processors or processing units, associated memory, and other hardware and/or software.

In the illustrated example, the fluid analyzer module 312 includes a spectrometer to measure, among other things, the optical density (OD) of formation fluid samples. In other example implementations in which measurements (e.g., density measurements, nuclear magnetic resonating (NMR) measurements, resistivity measurements, capacitance measurements, etc.) other than or in addition to OD measurements are used, the fluid analyzer module 312 may be replaced or supplemented with other types of suitable sensors (e.g., a reflection/fluorescence sensor, NMR sensors, density sensors, resistivity sensors, capacitance sensors, etc.).

Once at a desired depth, the example tool 300 of FIG. 10 is used to obtain a formation fluid sample and/or make one or more measurements of a collected and/or passing fluid sample. The example tool 300 has any number and/or type(s) of probes, and/or fluid inlets and/or ports (one of which is designated by reference numeral 314), that are selectively extendable from the tool 300, as well as a selectively extendable anchoring member 316 on the opposite side of the tool 300. The example probe 314 of FIG. 10 extends from the tool 300 and seals against a borehole wall 318 so that the probe 314 is in fluid communication with the formation 302. The example tool 300 may also include one or more pumps (not shown) to pump formation fluids from the formation 302 into the tool 300 and/or to pump formation fluids from the tool 300 into the borehole 304.

Formation fluids sampled by the tool 300 may be contaminated with mud filtrate. That is, the formation fluids may be contaminated with the filtrate of a drilling fluid that seeps into the formation 302 during the drilling process. Thus, when fluids are withdrawn from the formation 302, these extracted fluids may initially contain mud filtrate. In some examples, formation fluids are withdrawn from the formation 302 and pumped into the borehole 304 or into a large waste chamber (not shown) in the tool 300 until the fluid being withdrawn becomes sufficiently clean. A clean fluid sample has a concentration of mud filtrate that is acceptably low such that the fluid substantially represents native (i.e., naturally occurring) formation fluid. Once the fluid being withdrawn is sufficiently clean, a sample fluid may be further analyzed, measured, and/or collected for analysis. In the illustrated example, the tool 300 is provided with a fluid store module 320 to store collected fluid samples.

The fluid analyzer module 312 may include one or more sensors to provide measurements as formation fluid is pumped (e.g. during a clean-up phase). In the case of optical sensors (e.g., a spectrometer), optical density values received from these sensors may be used to compute a formation fluid composition. Also, extrapolation techniques may be used in combination with fluid measurements made during a clean-up phase to predict the fluid properties that would be exhibited by pristine fluid samples. Although the formation testing tool 300 is provided with the fluid store 320 to bring samples to the surface for subsequent analysis, the fluid analyzer module 312 can be advantageously used to measure fluid properties of the formation fluid while the formation fluid is being extracted downhole from the formation 302. Measuring the extracted formation fluid downhole (i.e., in situ) allows the formation fluid to remain at substantially the same pressure and temperature and to maintain substantially the same fluid component mixture state it would have while in the formation 302. In contrast, bringing the formation fluid samples to the surface changes the temperature, pressure, and other characteristics of the fluid such that fluid property measurements performed at the surface yield different results than if the same measurements were performed downhole. Thus, measuring the extracted formation fluid downhole provides measurement values that are relatively more representative of the properties or characteristics of the formation fluid in the formation 302.

While the downhole tool 200 of FIG. 9 and the downhole tool 300 of FIG. 10 are shown provided with one probe, more probes may be provided in other example implementations. Further, in alternative example implementations, inflatable packers can be used instead of the probes to establish fluid connections with formations and draw fluid samples. In addition, the example methods and apparatus described herein are not limited to a particular conveyance type and may be implemented in connection with different conveyance types including, for example, coiled tubing, wired-drill-pipe, and/or other conveyance means known in the industry.

Figure 11:
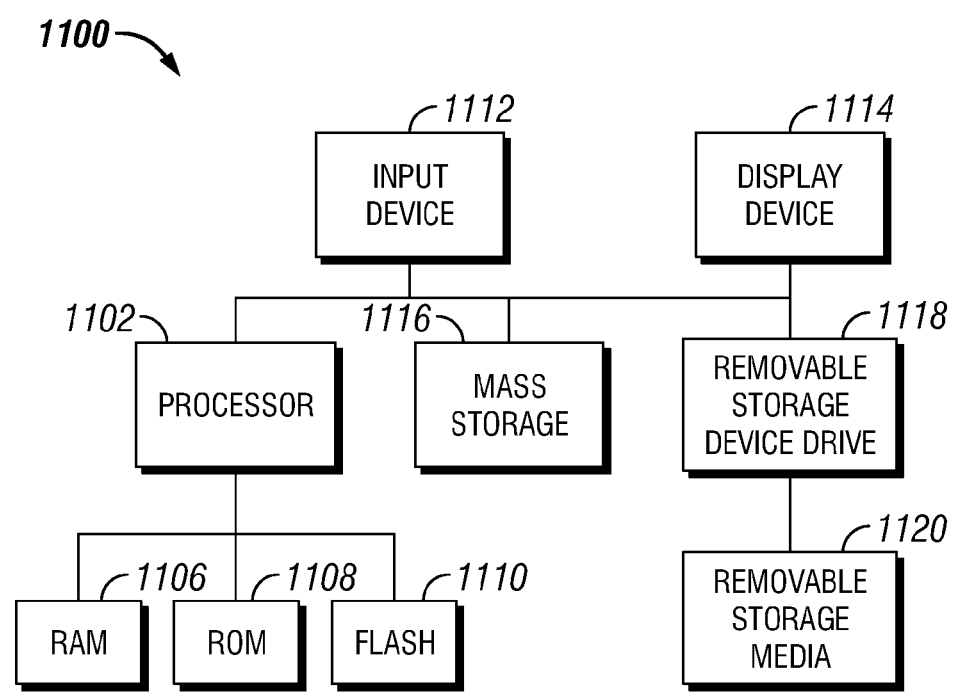
FIG. 11 is a block diagram of an example processing unit that may be used to implement the example methods and apparatus described herein.

FIG. 11 is a block diagram of an example computing system 1100 that may be used to implement the example methods and apparatus described herein. For example, the computing system 1100 may be used to determine whether a coating is present on one or more of the windows of the spectrometer 420 and/or the reflection/fluorescence sensor 424 from measurements made by the spectrometer 420 and/or the reflection/fluorescence sensor 424. In one example, the controller 432 may determine that the spectrometer 420 and reflection/fluorescence sensor 424 windows are coated based on contradictory measurements. In the example, the spectrometer 420 determines that the GOR is above a particular threshold to indicate that the fluid sample is a gas. However, the spectrometer 420 also determines that the optical density of the fluid sample is very high (e.g., approximately 3.0).

Further the computing system 1100 may be used to implement the above-described logging and control system 160 and the controller and/or processing system 230 of FIG. 9. Alternatively, portions of the computing system 1100 may be used to implement the above-described the controller and/or processing system 308 and/or 310 of FIG. 10. The example computing system 1100 may be, for example, a conventional desktop personal computer, a notebook computer, a workstation or any other computing device. A processor 1102 may be any type of processing unit, such as a microprocessor from the Intel® Pentium® family of microprocessors, the Intel® Itanium® family of microprocessors, and/or the Intel XScale® family of processors. Memories 1106, 1108 and 1110 that are coupled to the processor 1102 may be any suitable memory devices and may be sized to fit the storage demands of the system 1100. In particular, the flash memory 1110 may be a non-volatile memory that is accessed and erased on a block-by-block basis. As described before, the processor 1102, and the memories 1106, 1108 and 1110 may additionally or alternatively be implemented downhole, for example, to store, analyze, process, and/or compress test and measurement data (or any other data) acquired by the DFA tool 400 and/or to control the operations of the DFA tool 400.

An input device 1112 may be implemented using a keyboard, a mouse, a touch screen, a track pad or any other device that enables a user to provide information to the processor 1102.

A display device 1114 may be, for example, a liquid crystal display (LCD) monitor, a cathode ray tube (CRT) monitor or any other suitable device that acts as an interface between the processor 1102 and a user. The display device 1114 as pictured in FIG. 11 includes any additional hardware required to interface a display screen to the processor 1102.

A mass storage device 1116 may be, for example, a conventional hard drive or any other magnetic or optical media that is readable by the processor 1102.

A removable storage device drive 1118 may, for example, be an optical drive, such as a compact disk-recordable (CD-R) drive, a compact disk-rewritable (CD-RW) drive, a digital versatile disk (DVD) drive or any other optical drive. It may alternatively be, for example, a magnetic media drive. A removable storage media 1120 is complimentary to the removable storage device drive 1118, inasmuch as the media 1120 is selected to operate with the drive 1118. For example, if the removable storage device drive 1118 is an optical drive, the removable storage media 1120 may be a CD-R disk, a CD-RW disk, a DVD disk or any other suitable optical disk. On the other hand, if the removable storage device drive 1118 is a magnetic media device, the removable storage media 1120 may be, for example, a diskette or any other suitable magnetic storage media.

Although example methods, apparatus and articles of manufacture have been described herein, the scope of coverage of this patent is not limited thereto. On the contrary, this patent covers every apparatus, method and article of manufacture fairly falling within the scope of the appended claims either literally or under the doctrine of equivalents.

What is claimed is:

1. A method to detect a coating on a downhole fluid sensor, comprising:
   measuring a gas/oil ratio of a fluid sample;
   causing the fluid sensor to make at least one fluid sample measurement; and
   processing the measured gas/oil ratio of the fluid sample and the at least one fluid sample measurement to determine whether the at least one fluid sample measurement is indicative of a film coating on a fluid sensor interface with the sampled fluid, wherein the measured gas/oil ratio is used to determine the presence of the film coating.

2. A method as defined in claim 1, wherein causing the fluid sensor to make at least one fluid sample measurement comprises measuring a fluid sample for at least one of an optical density parameter, a color absorption parameter, a scattering parameter, a water fraction parameter, a reflection parameter or a fluorescence parameter.

3. A method as defined in claim 2, wherein measuring a gas/oil ratio of a fluid sample further comprises determining whether the gas/oil ratio is within a predetermined range.

4. A method as defined in claim 3, wherein said processing comprises comparing the optical density parameter and the color absorption parameter to corresponding threshold values typical of gas.

5. A method as defined in claim 1, wherein the fluid sample measurement is indicative a film coating on the fluid sensor when the fluid sample measurement is contradictory to the measured gas/oil ratio.

6. A method as defined in claim 5, wherein the at least one fluid sample measurement is obtained with an optical reflection/fluorescence sensor or an optical spectrometer.

7. A method as defined in claim 1, wherein causing the fluid sensor to make at least one fluid sample measurement comprises measuring a plurality of color absorption parameters for each of a plurality of wavelengths.

8. A method as defined in claim 7, wherein said processing comprises determining that a first color absorption parameter associated with a first wavelength corresponds to a higher optical density than an optical density associated with a second color absorption parameter associated with a second wavelength that is longer than the first wavelength.

9. A method as defined in claim 7, wherein said processing comprises determining that the plurality of color absorption parameters correspond to an absorption pattern of a substance indicative of the coating substance.

10. A method as defined in claim 1, wherein said processing comprises determining whether the at least one fluid sample measurement is within a range of values determined by the fluid type.

11. A method as defined in claim 1, further comprising pumping the fluid sample into a fluid analyzer and wherein said processing comprises determining that the at least one fluid sample measurement is substantially unresponsive to the pumping of the fluid sample.

12. A method as defined in claim 1 performed while drilling.

13. A method to detect a coating on a window of a downhole fluid analyzer, comprising: measuring an optical density parameter of a fluid sample; measuring a color absorption parameter of the fluid sample for each of a plurality of color channels; determining a gas/oil ratio of the fluid sample; and processing the optical density parameter, the color adsorption parameter, and the gas/oil ratio to determine whether there is a coating on the window of the fluid analyzer; determining a water fraction of the fluid sample and comparing the water fraction to a predetermined threshold and wherein said processing further comprises processing a comparison of the water fraction and the predetermined threshold to determine whether there is a coating on the window of the fluid analyzer.

14. A method as defined in claim 13, further comprising determining a reflection/fluorescence parameter associated with the fluid sample and wherein said processing further comprises processing the reflection/fluorescence parameter to determine whether there is a coating on the window of the fluid analyzer.

15. A method as defined in claim 13, wherein determining that there is a coating on the window is further based on at least two of the parameters having contradictory indications.

16. A method as defined in claim 13, wherein said processing further comprises:
    performing a first comparison of the optical density parameter with a predetermined value;
    performing a second comparison of color absorption parameters with a predetermined color absorption pattern; and
    wherein determining that there is a coating on the window of the fluid analyzer is based on the first and second comparisons.

17. A method as defined in claim 16, wherein performing a second comparison of color absorption parameters with a predetermined color absorption pattern comprises determining whether optical density decreases as wavelength increases.

18. A method as defined in claim 13, further comprising pumping the fluid sample into the fluid analyzer and wherein said processing to determine whether there is a coating on the window comprises determining that at least one of the optical density parameter or the water fraction parameter is substantially unresponsive to the pumping of the fluid sample.

* * * * *